United States Patent [19]

Wilk

[11] Patent Number: 5,217,453
[45] Date of Patent: Jun. 8, 1993

[54] AUTOMATED SURGICAL SYSTEM AND APPARATUS

[76] Inventor: Peter J. Wilk, 185 West End Ave., New York, N.Y. 10023

[21] Appl. No.: 682,002

[22] Filed: Apr. 8, 1991

Related U.S. Application Data

[63] Continuation-in-part of Ser. No. 670,720, Mar. 18, 1991.

[51] Int. Cl.⁵ .............................................. A61B 17/36
[52] U.S. Cl. ...................................... 606/7; 606/159; 604/95
[58] Field of Search .................. 128/4, 6; 606/7, 159, 606/180; 604/95, 159

[56] References Cited

U.S. PATENT DOCUMENTS

| | | |
|---|---|---|
| 3,834,392 | 9/1974 | Lampman et al. . |
| 4,343,300 | 8/1982 | Hattori . |
| 4,499,895 | 2/1985 | Takayama . |
| 4,572,198 | 2/1986 | Codrington . |
| 4,573,452 | 3/1986 | Greenberg . |
| 4,601,705 | 7/1986 | McCoy ............................ 604/95 |
| 4,621,618 | 11/1986 | Omagari . |
| 4,672,963 | 6/1987 | Barken . |
| 4,758,222 | 7/1988 | McCoy . |
| 4,785,806 | 11/1988 | Decklebaum ..................... 606/7 |
| 4,788,975 | 12/1988 | Shturman et al. ................. 606/7 |
| 4,790,813 | 12/1988 | Keasey ......................... 606/159 X |
| 4,791,934 | 12/1988 | Brunnett . |
| 4,875,897 | 10/1989 | Lee ................................ 606/7 X |
| 4,887,605 | 12/1989 | Angelsen et al. ................ 606/7 X |
| 4,974,607 | 12/1990 | Miwa .............................. 128/904 |
| 4,996,975 | 3/1991 | Nakamura . |
| 5,078,714 | 1/1992 | Katims ........................... 604/95 X |
| 5,104,392 | 4/1992 | Kittrell et al. .................. 606/7 X |
| 5,225,888 | 6/1992 | Howard et al. .................. 604/95 X |

FOREIGN PATENT DOCUMENTS

| | | |
|---|---|---|
| 0079524 | 5/1983 | European Pat. Off. . |
| 0467459 | 11/1992 | European Pat. Off. .............. 606/7 |
| 3431022 | 3/1985 | Fed. Rep. of Germany . |
| 9101687 | 2/1991 | PCT Int'l Appl. ................. 606/7 |

Primary Examiner—Gene Mancene
Assistant Examiner—Nicholas D. Lucchesi
Attorney, Agent, or Firm—R. Neil Sudol; Henry D. Coleman

[57] ABSTRACT

A surgical system comprises an endoscopic instrument, a camera on the endoscopic instrument for obtaining video images of internal body tissues inside a patient's body via the endoscopic instrument, and a transmitter operatively connected to the camera for transmitting, over a telecommunications link to a remote location beyond a range of direct visual contact with the patient's body, a video signal encoding the video image. A receiver is provided for receiving actuator control signals from the remote location via the telecommunications link. The receiver feeds the signals to a robot actuator mechanism for controlling that mechanism to operate a surgical instrument insertable into the patient's body.

11 Claims, 3 Drawing Sheets

AUTOMATED SURGICAL SYSTEM AND APPARATUS

CROSS-REFERENCE TO A RELATED APPLICATION

This application is a continuation-in-part of application Ser. No. 670,720 filed Mar. 18, 1991.

BACKGROUND OF THE INVENTION

This invention relates to a surgical system and a related method. More particularly, this invention relates to an endoscopic or laparoscopic surgical method and apparatus.

The advantages of laparoscopic and endoscopic surgical methods have become increasingly apparent to surgeons and to society at large. Such surgical techniques are minimally invasive, require less operating time, and reduce trauma and convalescence time required after surgery is completed. In general, noninvasive surgery using laparoscopic and endoscopic techniques will be used more and more frequently to reduce hospital and surgical costs.

In endoscopic and laparoscopic surgery, the surgeon is provided with visual information through optical fibers extending through the endoscope or laparoscope. Sometimes, the visual information is provided to the surgeon and other operating room personnel via video monitors which show images obtained by small video cameras (charge coupled devices) at the distal ends of the endoscopes or laparoscopes. Although this video information may be transmitted to other rooms in the hospital or other institutional clinical setting, the surgeon is always present in the operating room to manipulate the surgical instruments and thereby perform the surgical operation in response to the video images on a monitor.

The use of video images provides an opportunity for further reductions in the expense and time required for surgery.

OBJECTS OF THE INVENTION

An object of the present invention is to provide a method and apparatus for performing angioplastic surgery which reduces surgical costs.

Another, more particular, object of the present invention is to provide a method and apparatus which facilitates the performance such of operations by surgeons from all over the world.

SUMMARY OF THE INVENTION

A surgical method in accordance with the present invention is used with an X-ray or fluoroscopic device and an angioplastic instrument including a tubular member and an operating tool for removing a blockage in the blood vessel. The method comprises the steps of (a) inserting the instrument into a blood vessel of a patient's body, (b) obtaining a video image of structure inside the blood vessel via the X-ray or fluoroscopic device, (c) transmitting, over a telecommunications link, a video signal encoding the video image to a remote location beyond a range of X-ray penetration from said X-ray or flouroscopic device, (d) receiving actuator control signals from the remote location via the telecommunications link, and (e) automatically actuating the operating tool in response to the received actuator control signals.

Pursuant to another feature of the present invention, the operating tool includes a source for generating a laser beam and an optical fiber for guiding the laser beam from the source to a distal end of the instrument. Alternatively, the operating tool includes a blade at a distal end of the instrument. As another alternative embodiment of the invention, the operating tool includes an expandable balloon at a distal end of the instrument and pressurized supply for inflating the balloon inside the vessel.

Pursuant to another feature of the present invention, the step of obtaining the video image includes the step of injecting a radiographic fluid into the vessel via the instrument. Preferably, the step of injecting is performed in response to a signal received from the remote location via the telecommunications link.

Pursuant to another feature of the present invention, additional control signals are received from the remote location via the telecommunications link for controlling an automatic shifting of the angioplastic operating instrument relative to the blood vessel.

The imaging device may take the form of a fluoroscope or X-ray sensing apparatus.

Pursuant to a further feature of the present invention, the system includes a dispenser device for injecting a radiographic fluid into the vessel via the instrument in response to a signal received by the receiver from the remote location.

Pursuant to yet a further feature of the present invention, a translation drive is operatively connected to the tubular member and to the receiver for automatically shifting the tubular member relative to the blood vessel in response to a signal received by the receiver from the remote location.

DETAILED DESCRIPTION

Figure 1:
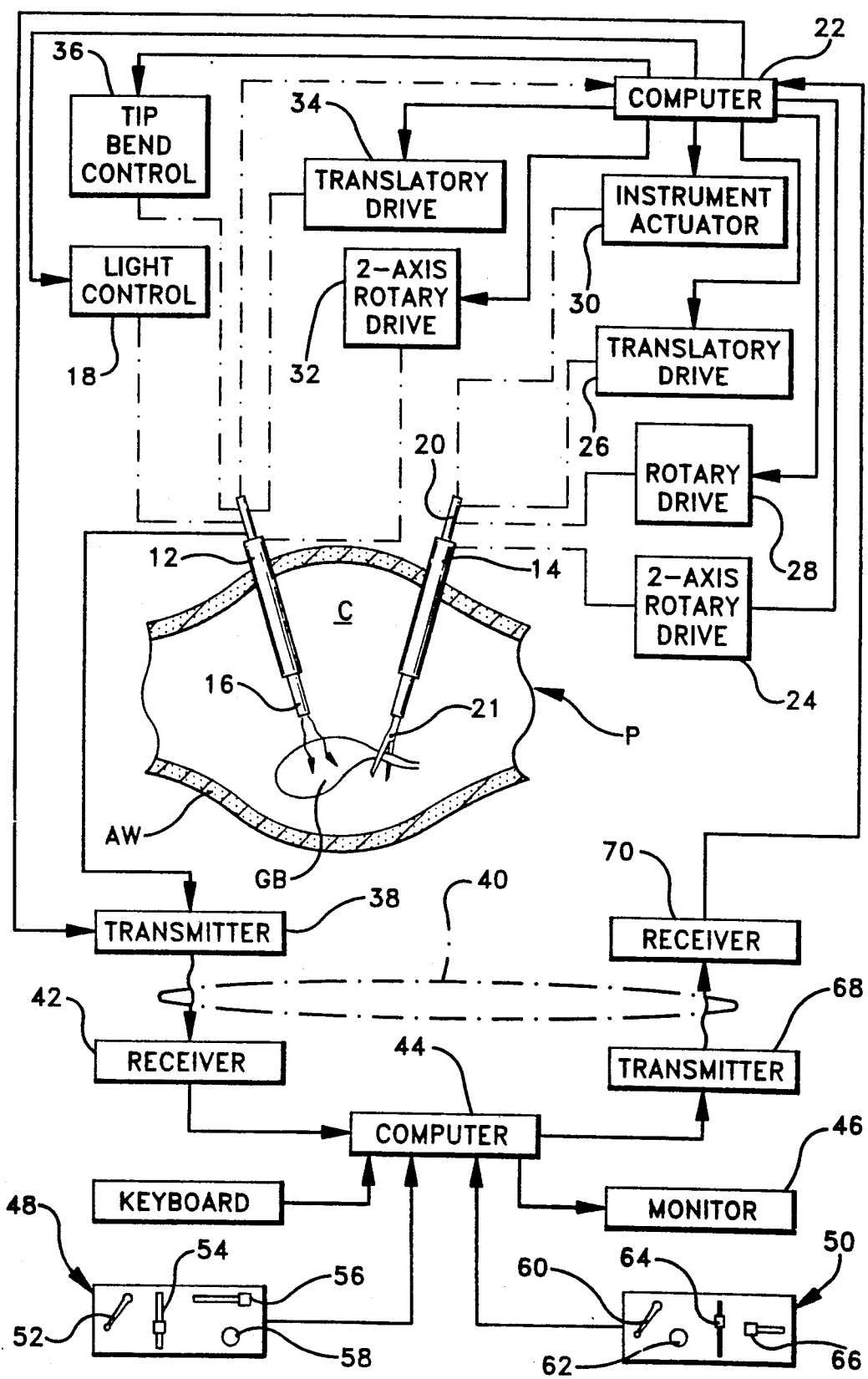
FIG. 1 is a diagram of a remotely controlled operating system for performing laparoscopic surgery

As illustrated in FIG. 1, a patient P undergoing laparoscopic surgery, for example, removal of a gall bladder GB, has an internal body cavity C pressurized with air to distend the abdominal wall AW. The abdominal wall is pierced with a trocar (not shown) and a plurality of hollow tubes 12 and 14 are inserted through the abdominal wall to provide passage for the operating instruments. One such instrument is an endoscopic type device, namely, a laparoscope 16 which includes an optical fiber (not illustrated) for delivering optical radiation OR from a light source or control component 18 to the surgical site. Another instrument takes the form of a forceps instrument 20 or other device for manipulating and/or severing internal body tissues such as gall bladder GW.

Forceps instrument 20 includes a pair of forceps jaws 21 whose position inside body cavity C is controlled by a computer 22 via a two-axis rotary drive 24 and a translatory drive 26. Rotary drive 24 is operatively connected to tube 14 for pivoting the tube at its point of penetration through abdominal wall about two axes of rotation. In response to signals from computer 22, translatory drive 26 slides forceps instrument 20 longitudinally through tube 14.

The orientation of forceps jaws 21 is controlled by computer 22 via a one- or two-axis rotary drive 28, while forceps jaws 21 are alternately opened and closed by an actuation mechanism 30 in response to control signals from computer 22.

The position of a distal tip of laparoscope 16 inside body cavity C is controlled by computer 22 via a two-axis rotary drive 32 mechanically linked to tube 14 and a translatory drive 34 operatively coupled with laparoscope 16. Translatory drive 34 varies the degree of insertion of laparoscope 16 through tube 12, while rotary drive 32 swings tube 12 about two axes of rotation.

The intensity and/or the hue of optical radiation OR is controlled by computer 22 via light source or control component 18. In addition, in the event that laparoscope 16 is flexible, the curvature of the distal end portion of the laparoscope is modifiable by computer 22 via a bend control component 36.

Laparoscope 16 incorporates a charge coupled device (not illustrated) for converting optical incoming optical radiation, reflected from internal body tissues inside cavity C, to a video signal. That video signal, encoding a video image, is transmitted from laparoscope 16 to a transmitter 38 and optionally to computer 22.

Transmitter 38 in turn transmits the video signal over a telecommunications link 40 to a remote receiver 42 which relays the video signal to another computer 44. Computer 44 uses the incoming video signal to display on a monitor 46 an image of the internal body tissues of patient P.

Connected to computer 44 are at least two sets of input devices 48 and 50 operated by a surgeon to remotely control a surgical procedure. More specifically, input device 48 includes a joy stick 52 for controlling the operation of rotary drive 32, a slide switch 54 for controlling the operation of translatory drive 34, another slide switch 56 for controlling light source or control component 18 to modify light intensity, and a dial or knob 58 for controlling bend control component 36 to change the angle of inclination of the distal end portion of laparoscope 16.

Input device 50 includes a joy stick 60 for controlling the operation of rotary drive 24, a dial or knob 62 for controlling rotary drive 28, a slide switch 64 for controlling translatory drive 26, and another slide switch 66 for controlling instrument actuator 30.

Signals from input devices 48 and 50 are encoded by computer 44 and sent to computer 22 via a transmitter 68, telecommunications link 40, and a receiver 70. Computer 22 then uses the incoming signals to provide control signals to the various drives and other components at the site of the surgery.

It is to be understood, of course, that surgeons and other personnel are present in the operating room at the time of surgery to oversee and supervise the proper operation of the equipment. These personnel may communicate with the remote surgeon via computers 22 and 44 and telecommunications link 40 and/or through other telecommunications linkages such as the telephone network. To facilitate local supervision, computer 22 is connected to a local monitor (not shown) for displaying the video images garnished by laparoscope 16 and, for example, for displaying alphanumeric codes indicating the positions and operating statuses of the instruments, e.g., light source or control component 18 and forceps instrument 20. Such information may also be transmitted by computer 22 to computer 44 over transmitter 38, link 40 and receiver 42 and displayed on monitor 46. Other parameters regarding the condition of patient P, such as temperature, heart rate, oxygen consumption, brain wave activity, and blood sugar level, may also be automatically sensed, encoded and transmitted to remote computer 44 for providing the lead surgeon in real time with all information necessary for performing the surgery successfully.

Figure 2:
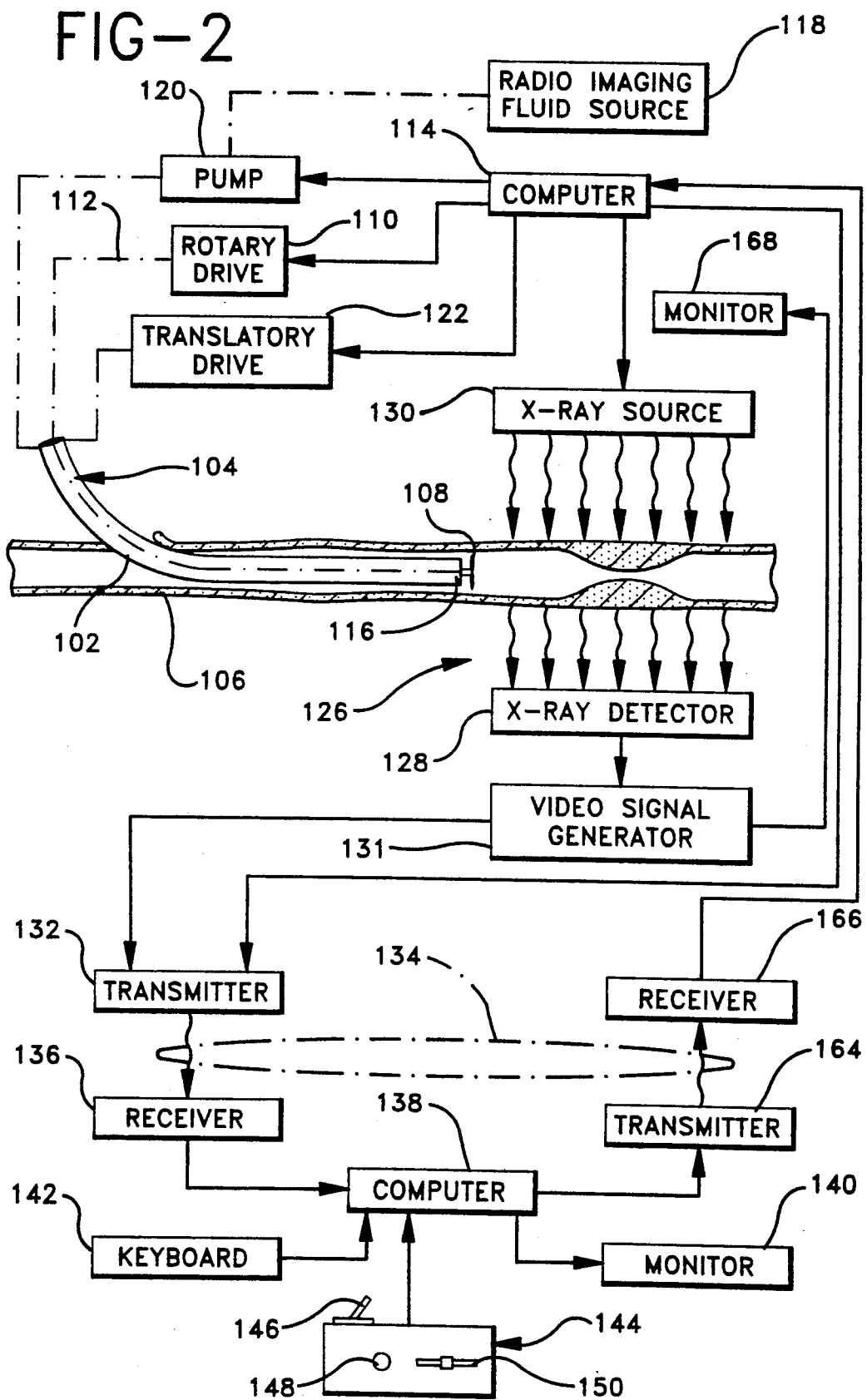
FIG. 2 is a diagram of another remotely controleld system, in accordance with the present invention, for performing angioplastic surgery.

As illustrated in FIG. 2, a tubular member 102 of an angioplastic operating instrument 104 is inserted into a blood vessel 106 of a patient. At a distal end, instrument 104 includes a rotary blade 108 operatively linked to a drive 110 via a transmission member 112. Rotary drive 110 is operated or energized under the control of a computer 114.

At its distal end, instrument 104 is further provided with an opening 116 for injecting into vessel 106 a radiographic or radio-imaging fluid from a source 118. The injection operation is implemented by a pump 120 in response to actuating signals from computer 114.

Computer 114 controls the degree that tubular member 102 is inserted into vessel 106 by actuating a translatory drive 122 operatively coupled to the tubular member.

The location of a blockage 124 inside vessel 106 is detectable via an electromagnetic imaging device 126 exemplarily taking the form of an X-ray detector 128 receiving X-rays from a source 130 via that part of the patient including vessel 106 and blockage 124. Blockage 124 is highlighted through the injection of the radio-imaging fluid from source 118. Alternatively, the radio-imaging fluid may be radioactive, electromagnetic imaging device 126 taking the form of a fluoroscope.

Upon the insertion of tubular member 102 into vessel 106, electrical signals encoding video images of structure inside vessel 106, such as blockage 124, are produced by a signal generator 131 connected at an output of X-ray detector 128. The video signals are sent via a transmitter 132 and a telecommunications link 134 to a remote receiver 136 which relays the video signal to a computer 138. Computer 138 uses the incoming video signal to display on a monitor 140 an image of structure internal to vessel 106. Transmitter 132, telecommunications link 134 and receiver 136 are also used to transmit data from local computer 114 to remote computer 138.

A keyboard 142 and an optional switchboard or console 144 are connected to computer 138 for enabling a surgeon at a remote location to control the operation of instrument 104. More particularly, console 144 includes a toggle switch 146 for controlling the operation of rotary drive 110, a knob 148 for controlling the operation of pump 120, and a slide switch 150 for determining the distance that tubular member 102 is inserted in vessel 106. The remote surgeon manipulates switches 146 and 150 and knob 148 in response to video images on monitor 140. Those images are themselves changed by the surgeon by shifting tubular member 102 further along vessel 106 and by periodically injecting radio-imaging fluid into the vessel from source 118.

Figure 3:
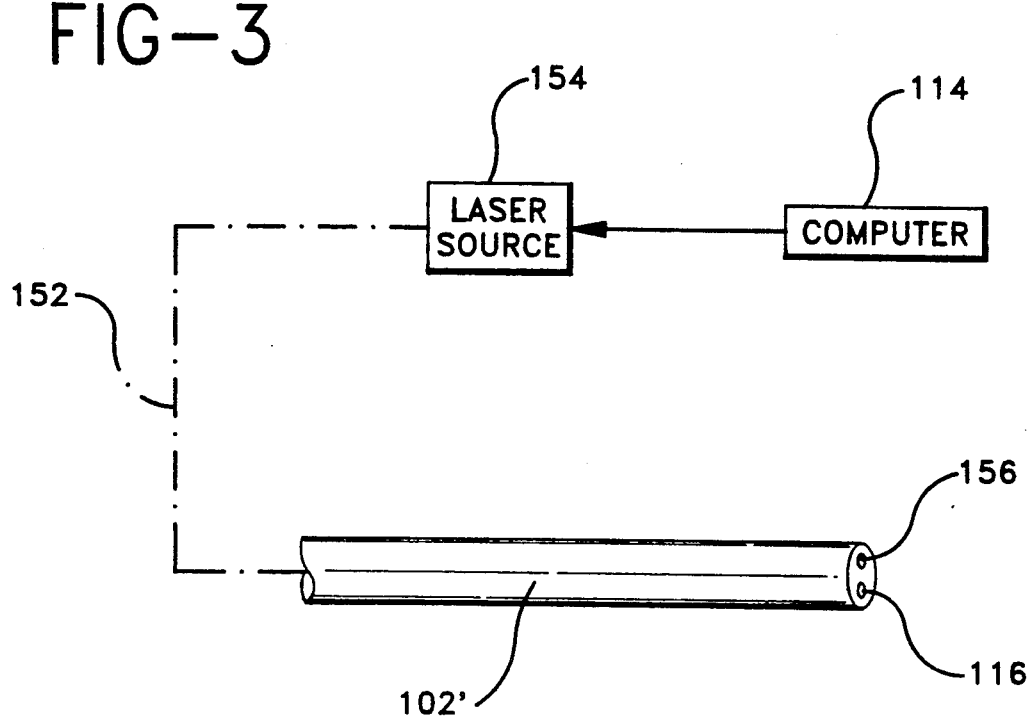
FIG. 3 is a diagram of a modified portion of the system of FIG. 2.
Figure 4:
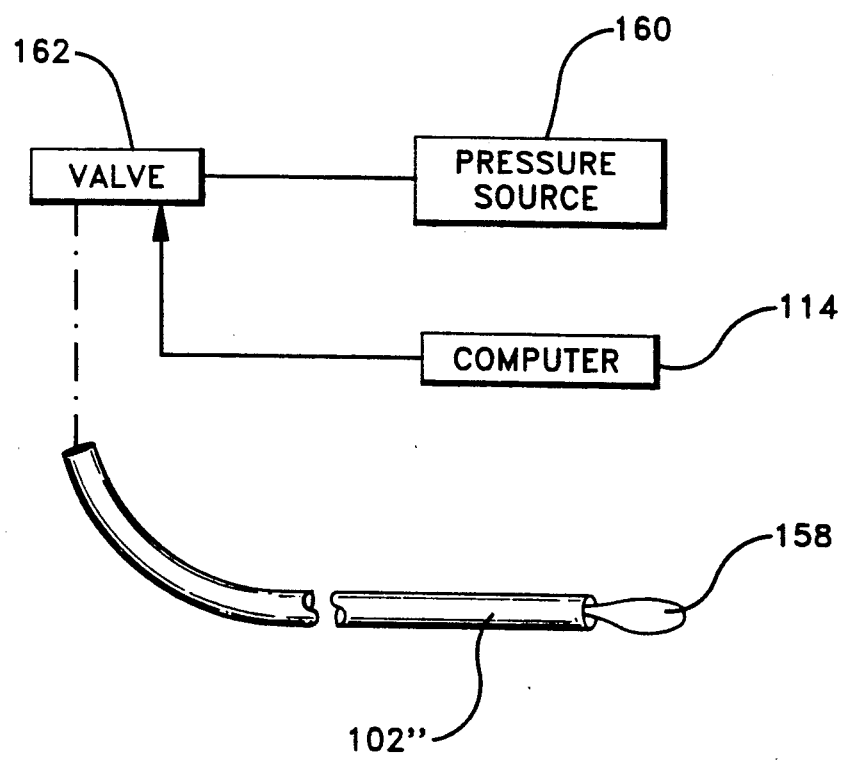
FIG. 4 is a diagram of a portion of the system of FIG. 2, modified in another way.

FIG. 3 illustrates a modification of the system of FIG. 2 wherein the surgical tool in a tubular angioplastic surgical member 102' takes the form of an optical fiber 152 for guiding a laser beam from a source 154 to an exit 156 at the distal end of the tubular member. FIG. 4 depicts an alternative modification wherein the blockage removal tool takes the form of an inflatable balloon or bladder 158 disposed at a distal end of an angioplastic surgical member 102". Bladder 158 is expanded by pressure released from a pressurized gas source 160 by opening a valve 162 in response to signals from computer 114. Of course, computer 114 operates in response to signals from computer 138.

As discussed hereinabove with reference to FIG. 1, it is understood that surgeons and other personnel are present in the operating room at the time of surgery to oversee and supervise the proper operation of the equipment. These personnel may communicate with the remote surgeon via computers 114 and 138 and transmitters 132 and 164, receivers 136 and 166, and telecommunications link 13 and/or through other telecommunications linkages such as the telephone network. To facilitate local supervision, computer 114 is connected to a local monitor 168 for displaying the video images obtained by electromagnetic imaging device 126 and, for example, for displaying alphanumeric codes indicating the positions and operating statuses of the instruments. Such information may also be transmitted by computer 114 to computer 138 over transmitter 132, link 134 and receiver 136 and displayed on monitor 140. Other parameters regarding the condition of patient P, such as temperature, heart rate, oxygen consumption, brain wave activity, and blood sugar level, may also be automatically sensed, encoded and transmitted to remote computer 138 for providing the lead surgeon in real time with all information necessary for performing the surgery successfully.

Although the invention has been described in terms of particular embodiments and applications, one of ordinary skill in the art, in light of this teaching, can generate additional embodiments and modifications without departing from the spirit of or exceeding the scope of the claimed invention. For example, other kinds of optically guided surgery may be performed from a remote location via the computer aided automation of the instant invention, Accordingly, it is to be understood that the drawings and descriptions herein are proferred by way of example to facilitate comprehension of the invention and should not be construed to limit the scope thereof.

What is claimed is:

1. A surgical method, comprising the steps of:
    inserting a flexible tubular instrument into a blood vessel of a patient located in a surgical operating area, said instrument being provided with operating means for removing a blockage in said blood vessel;
    obtaining a video image of structure inside said blood vessel via an X-ray or fluoroscopic device also located at least partially in said operating area;
    transmitting a video signal encoding said video image to a remote location removed from said operating area and beyond a range of X-ray penetration from said X-ray or fluoroscopic device;
    receiving actuator control signals from said remote location; and
    automatically shifting said instrument longitudinally relative to said blood vessel to change a degree of insertion of said instrument into said blood vessel in response to the received actuator control signals.

2. The method recited in claim 1 wherein said operating means includes source means for generating a laser beam and an optical fiber for guiding said laser beam from said source means to a distal end of said instrument, further comprising the steps of energizing said source means from said remote location to generate said laser beam and transmitting said laser beam along said optical fiber to the distal end of said instrument.

3. The method recited in claim 1 wherein said operating means includes a blade at a distal end of said instrument, further comprising the step of actuating said blade from said remote location to execute a cutting operation in said blood vessel.

4. The method recited in claim 1 wherein said operating means includes an expandable balloon at a distal end of said instrument and means for inflating said balloon inside said vessel, further comprising the step of actuating, from said remote location, said means for inflating.

5. The method recited in claim 1 wherein said step of obtaining includes the step of injecting a radiographic fluid into said vessel via said instrument, said step of injecting being controlled from said remote location.

6. The method recited in claim 5 wherein said step of injecting is performed in response to a signal received from said remote location via said telecommunications link.

7. The method recited in claim 1, further comprising the steps of receiving additional control signals from said remote location via said telecommunications link and automatically actuating said operating means in response to said additional control signals.

8. A surgical system comprising:
    an angioplastic operating instrument including a flexible tubular member insertable into a blood vessel of patient located in a surgical operating area, said instrument further including means for removing a blockage in said blood vessel;
    electromagnetic imaging means including an X-ray or fluoroscopic device also located at least partially in said operating area for generating a video image of structure inside said blood vessel;
    transmission means operatively connected to said imaging means for transmitting, to a remote location removed from said operating area and beyond a range of X-ray penetration from said X-ray or fluoroscopic device, a video signal encoding said video image;
    receiver means at said operating area for receiving actuator control signals from said remote location; and
    robot actuator means operatively connected to said instrument and said receiver means for shifting said instrument longitudinally relative to said blood vessel to change a degree of insertion of said instrument into said blood vessel in response to the actuator control signals received by said receiver means from said remote location.

9. The system recited in claim 8, further comprising means operatively connected to said instrument and said receiver means for injecting a radiographic fluid into said vessel via said instrument in response to a signal received by said receiver means from said remote location.

10. The system recited in claim 8, further comprising means operatively connected to said instrument and said receiver means for automatically actuating said means for removing in response to a signal received by said receiver means from said remote location.

11. A surgical system comprising:
    an angioplastic operating instrument including a flexible tubular member insertable into a blood vessel of a patient located in a surgical operating area, said instrument further including means for removing a blockage in said blood vessel;

electromagnetic imaging means including an X-ray or fluoroscopic device also located at least partially in said operating area for generating a video image of structure inside said blood vessel;

transmission means operatively connected to said imaging means for transmitting, to a remote location removed from said operating area and beyond a range of X-ray penetration from said X-ray or fluoroscopic device, a video signal encoding said video image;

receiver means at said operating area for receiving actuator control signals from said remote location;

robot actuator means operatively connected to said instrument and said receiver means for shifting said tubular member longitudinally relative to said blood vessel to change the degree of insertion of said instrument into said blood vessel in response to said control signals;

means operatively connected to said instrument and said receiver means for injecting a radiographic fluid into said vessel via said instrument in response to a signal received by said receiver means from said remote location; and means operatively connected to said instrument and said receiver means for automatically actuating said means for removing in response to a signal received by said receiver means from said remote location.

* * * * *